United States Patent [19]
Soffer et al.

[11] Patent Number: 5,914,434
[45] Date of Patent: Jun. 22, 1999

[54] SEPARATION OF LINEAR FROM BRANCHED HYDROCARBONS USING A CARBON MEMBRANE

[75] Inventors: Abraham Soffer, Arad; Jack Gilron; Haim Cohen, both of Beer-Sheva, all of Israel

[73] Assignee: Carbon Membranes, Ltd., Arava, Israel

[21] Appl. No.: 08/875,006

[22] PCT Filed: Jan. 16, 1996

[86] PCT No.: PCT/US96/00582

§ 371 Date: Aug. 29, 1997

§ 102(e) Date: Aug. 29, 1997

[87] PCT Pub. No.: WO96/22260

PCT Pub. Date: Jul. 25, 1996

[30] Foreign Application Priority Data

Jan. 16, 1995 [IL] Israel ........................................ 112349

[51] Int. Cl.[6] .................................................... C07C 7/144
[52] U.S. Cl. ........................................... 585/818; 210/651
[58] Field of Search ................................. 585/818; 96/4, 96/10; 423/445 R, 447.1; 210/651, 652, 653

[56] References Cited

U.S. PATENT DOCUMENTS

| | | | |
|---|---|---|---|
| 2,924,630 | 2/1960 | Fleck et al. | 585/818 |
| 4,685,940 | 8/1987 | Soffer et al. | 55/158 |
| 4,919,860 | 4/1990 | Schindler et al. | 264/29.1 |
| 5,069,794 | 12/1991 | Haag et al. | 210/650 |
| 5,104,425 | 4/1992 | Rao et al. | 55/16 |
| 5,107,059 | 4/1992 | Chen et al. | 585/818 |
| 5,288,304 | 2/1994 | Koros et al. | 95/45 |
| 5,431,864 | 7/1995 | Rao et al. | 264/29.5 |
| 5,507,860 | 4/1996 | Rao et al. | 96/12 |
| 5,695,818 | 12/1997 | Soffer et al. | 427/248.1 |

FOREIGN PATENT DOCUMENTS

| | | |
|---|---|---|
| 617 997 | 10/1994 | European Pat. Off. . |
| 621 071 | 10/1994 | European Pat. Off. . |
| 2 207 666 | 2/1989 | United Kingdom . |

*Primary Examiner*—Walter D. Griffin
*Attorney, Agent, or Firm*—Merchant, Gould, Smith, Edell, Welter & Schmidt, P.A.

[57] ABSTRACT

In a process for separating linear from branched hydrocarbons, the feed is brought in contact with a carbon membrane with critical size from 0.39 to 0.55 nm. The isomer with the larger size remains on the feed side. A membrane can be produced by activating a membrane by reacting it with oxygen and then with hydrogen.

5 Claims, 7 Drawing Sheets

SEPARATION OF LINEAR FROM BRANCHED HYDROCARBONS USING A CARBON MEMBRANE

FIELD OF THE INVENTION

The present invention relates to the separation of hydrocarbon isomers. More particularly the invention relates to a method of separating linear from branched hydrocarbons using carbon membranes, and to membranes therefor.

BACKGROUND OF THE INVENTION

Carbon membranes, their preparation and their use in the separation of various gases are known in the art, e.g., from U.S. Pat. No. 4,685,940, United Kingdom Patent No. 2,207,666 and European Patent No. 621,071. These membranes have been used for the separation of gas mixtures resulting from various processes. The most common process to which such methods have been applied are the separation of nitrogen and oxygen from air, but the separation of various binary gas mixtures including $N_2$, He, $O_2$ and $CO_2$ have also been carried out. Recently U.S. Pat. No. 5,104,425 has taught the separation of hydrogen from hydrocarbons using a carbon membrane, but those membranes separate based on differences in adsorptive power and surface diffusively of the different molecules such that often larger molecules (ethane and propane) permeate better than smaller molecules (hydrogen). The effect is often weakened or lost at higher temperatures. While the prior art, and specifically the above-mentioned U.S. Pat. No. 4,686,940, broadly mentions a pore size of the carbon membranes in the range of 2.5 Å to 5.0 Å, no membranes with pore sizes of above 3.8 Å have actually been prepared, because the separation problems contemplated by the prior art did not include difficult separations, such as the separation of isomers, and did not address gases having size which exceeds 3.8 Å. It is clear, therefore, that there is a need for a carbon membrane, characterized by a separation parameter which is solely dependent on the molecular dimension of the molecules to be separated; namely, the larger is the molecular dimension the lower is its permeability, and that said membrane should allow the separation of molecules, dimension of which is larger than 3.8 Å.

The art teaches different methods for separating branched from linear hydrocarbons, which do not involve carbon membranes. U.S. Pat. No. 5,069,794 and U.S. Pat. No . 2,924,630 disclose the use of molecular sieves zeolites, which are typically metallo alumino silicates. The pores in the crystalline structure of these molecular sieves have appropriate diameters to allow the separation. However, the preparation of said sieves is rather cumbersome, as it involves growing the porous crystalline structure over an appropriate substrate and then removing the layer of the crystalline zeolite, or providing the zeolitic barrier material the form of a filter cake, trapped between supporting surfaces. Furthermore, the performance of the carbon membrane according to the present invention is significantly better. For instance, the selectivity value for the separation of 2,2-dimethylbutane from n-hexane according to U.S. Pat. No. 5,069,794 is approximately 17. According to the present invention, a selectivity value, number of magnitudes of order higher, is obtained when separating 2,2-dimethylpropane from n-pentane.

SUMMARY OF THE INVENTION

It has now been found, and this is an object of the invention, that it is possible to employ carbon membranes not only to separate different gases, but also to separate isomers of hydrocarbons. This becomes possible because of the size sensitivity of the carbon membrane which can differentiate between normal and branched polymers, the former being of smaller critical dimension independent of the molecular weight and length. This is unlike other methods, such as fractional distillation, which is sensitive primarily to the molecular weight in a homologous series such as hydrocarbons. Thus while fractional distillation separates the petroleum hydrocarbon mixture mainly according to the molecular weight, the carbon membrane separates mainly branched from normal hydrocarbons.

This is important in the refining industry where the need for higher and various basic chemical precursors and the purification of the product streams from cat crackers requires separation of such isomers. The isomers of closet size are those of n-alkanes relative to their single branched isomers. (-iso), i.e. which contain a single tertiary carbon. In FIG. 1 it can be seen that there is a difference of 0.5 Å, between these two bids of isomers, independent of their length.

In another aspect, the invention is directed to a method of producing a carbon molecular sieve membrane which is suitable for the separation of hydrocarbon isomers, and to membranes obtained thereby.

Thus, according to the invention, linear and branched hydrocarbon isomers are separated from one another by using a carbon membrane having the appropriate critical size, comprised in the range 3.9 Å to 5.5 Å by bringing a mixture of two isomers to be separated into contact with one side of the membrane, applying a driving force across the membrane, typically by providing a pressure drop across the membrane, the higher pressure being on the feed mixture side, collecting a permeate richer in the isomer having the smaller size from the other side of the membrane, and collecting a retentate richer in the isomer having the larger size from the feed side of the membrane.

DETAILED DESCRIPTION OF THE INVENTION

Figure 1:
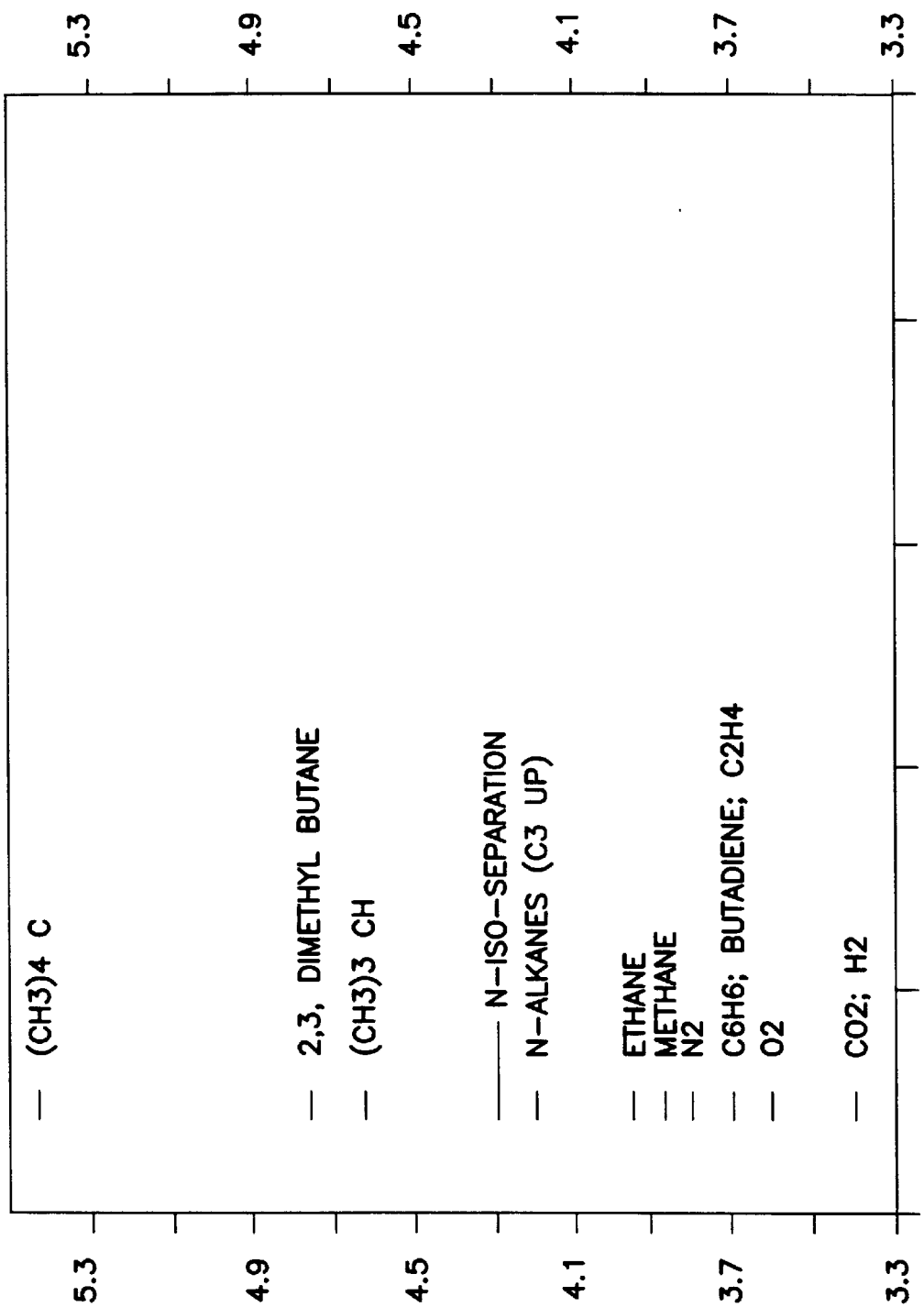
FIG. 1 shows the critical minimum molecular dimensions of different molecules.

The method for the separation of linear from branched hydrocarbon isomers according to the invention comprises the steps of:

selecting a carbon membrane having the appropriate critical size, comprised in the range 3.9 Å to 5.5 Å.

providing separating means between the two sides of the membrane, so that hydrocarbon molecules cannot move from one side of the membrane to the other, save through the membrane;

providing a mixture of two isomers to be separated and bringing the said mixture into contact with one side of the membrane;

applying a diving force across the membrane, typically by providing a pressure drop across the membrane, the higher pressure being on the feed mixture side;

collecting a permeate richer in the isomer having the smaller size from the other side of the membrane; and collecting a retentate richer in the isomer having the larger size from the feed side of the membrane.

As stated, the invention also encompasses a method of producing a membrane suitable for hydrocarbon isomers separation and the membrane produced thereby. As will be appreciated by the skilled person, such membranes can be manufactured by a variety of methods, and the invention is by no means limited to the use of membranes manufactured by any specific route. However, while not wishing to be bound to any particular preparation method, as stated above, it has been found that it is particularly advantageous to operate as follows. Firstly, a relatively closed membrane (viz., a membrane which has no substantial permeability of the selected hydrocarbons) is manufactured, e.g., as described in U.S. Pat. No. 4,685,940. If the membrane is not adequately closed it can be further closed by the art of chemical vapor deposition (CVD) as taught in U.S. Pat. application Ser. No. 08/213157, now abandoned. Then, the membrane is subjected to activation steps, involving reaction with oxygen followed by hydrogen, as will be described in detail hereinafter. Throughout the manufacture step $H_2/N_2$ and $O_2/N_2$ selectivities are measured The oxygen-hydrogen cycles are continued until the $H_2/N_2$, and then the $O_2/N_2$ selectivities drop significantly, at which time the permeability to hydrocarbons becomes appreciable and the membrane characteristics can be further adjusted to meet particular permeability/selectivity requirements for the system involved.

More generally, the three basic thermochemical treatments used in various orders and combinations for pore development are:

1. Activation treatment with oxygen at temperatures ranging from ambient to 500° C.
2. Treatment in vacuum, inert atmosphere, or reducing atmosphere such as noble gas, hydrogen, nitrogen or mixtures of them at the range of temperatures of 300° C.–1500° C.
3. Treatment by chemical vapor deposition (CVD) which coats the membrane surface with a layer. For example, an organic gas vapor that deposits a carbon residue on the membrane surface. In the Table in Example 1, 2,2-dimethyl propane was used as CVD material.

Figure 2A:
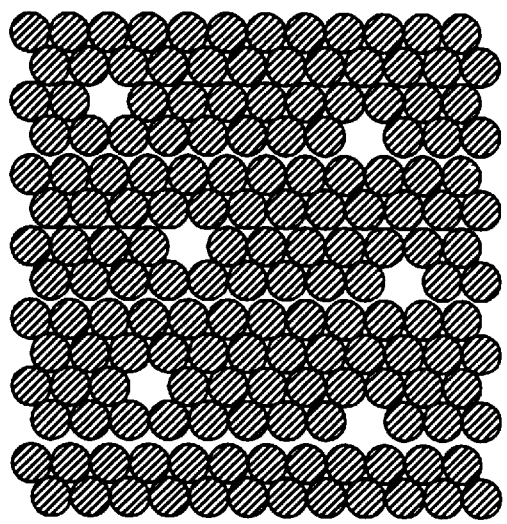
FIGS. 2a–2c illustrate the mechanism of self-activation leading, to inhomogeneous pore size distribution.
Figure 2B:
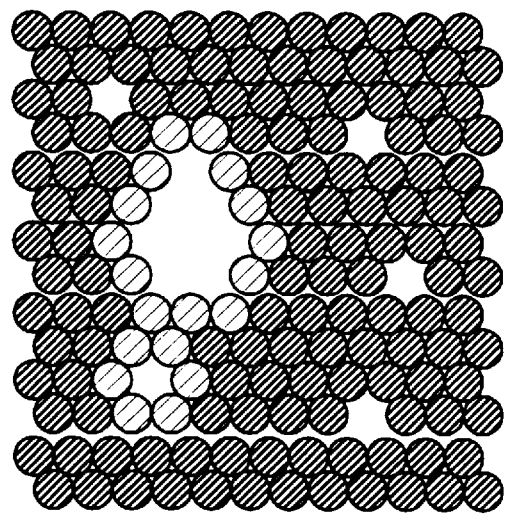

Thus, the process according to the above-described preferred embodiment of the invention utilizes $O_2$, $N_2$ and $H_2$ permeabilities as process control parameters in the manufacturing of the membranes of the invention. As will be appreciated by the skilled person, the major problem in the tailoring of membranes of this type is to know when both the pore mean size and the pore size-distribution function are in the desirable range. The procedure outlined above, which involves creating first a membrane having good $H_2/N_2$ and $O_2/N_2$ selectivities and then "ruining" such selectivities by the activation process with oxygen and hydrogen, leads to the formation of membranes which are suitable for the separation of isomers. This result is surprising since expanding the pores to wider ranges should also expand the nonhomogeneity of the pore size In other words, deeper pore size opening, namely, oxidation with oxygen, that is a controlled burnoff of the carbon material of the membrane, brings about significant weight losses and leads to a disrupted pore structure, and thus to nonhomoreneity. It is well known from elementary organic chemistry that when a certain carbon site in a molecule is attacked through a chemical reaction, the carbon in position to the attacked carbon will be more reactive, thus it is more likely to be attacked by further oxidation than a carbon that is remote from the previously attacked site. This effect is demonstrated in FIG. 2a–c.

Figure 2C:
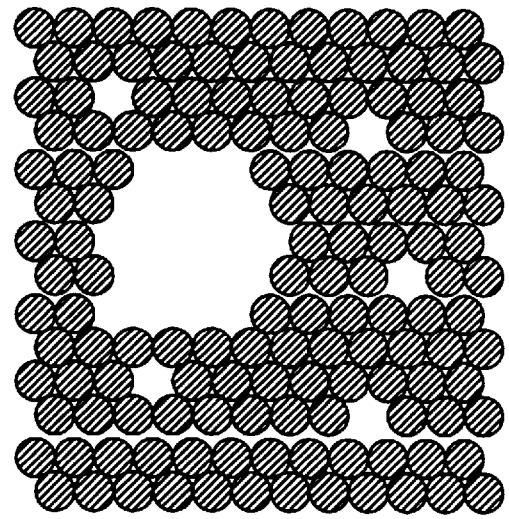

Accordingly, nonhomogeneous pore opening is expected to occur, i.e. when a pore is attacked by oxygen and enlarged, the neighboring carbon atoms become vulnerable and thus preferentially attacked further, so that the general tendency is enlarging pores that have been already enlarged in preference of unattacked pores, thus leading to nonhomogeneous pore opening which leads in turn to low selectivity, as shown in FIG. 2c.

Surprisingly, it was found that the selectivity-permeability combination of, e.g., normal pentane and 2-methyl butane isomers, is much better then the oxygen/nitrogen combination.

The invention is not meant to be limited to the separation of any specific isomer pairs. However, without derogating from the generality of the invention, the isomer pairs listed in Table I below, together with their critical sizes, are of particular interest for the purposes of the invention. According to their critical size, which is the smallest size that determines the permeability, the hydrocarbon may be divided into three categories:

1. Normal hydrocarbons where all the carbon atoms are bound to no more then two other carbon atoms in the molecule. These are the smallest in critical size. Their general formula is: $CH_3$—$(CH_2)n$—$CH_3$.
2. Isomers that contain at least one ternary carbon. Their general formula is $CH(-R_1)(-R_2)(-R_3)$ where the Rs are hydrocarbon entitles that are by themselves normal or containing ternary but not tertiary carbons. An example is 2-methyl butane.
3. Isomers that contain at least one tertiary carbon. Their general formula is $C(-R_1)(-R_2)(-R_3)(-R_4)$ where the Rs are hydrocarbon entities that are by themselves normal or containing ternary or tertiary carbons. An example is 2,2-dimethyl propane.

TABLE I

| Isomer Pair | Critical size range A |
| --- | --- |
| Normal | 4.20 |
| Ternary | 4.60–4.80 |
| Tertiary | 5.45–5.65 |

The number of isomers for a cell hydrocarbon increases rapidly with the number of carbon atoms. Thus, ethane ($CH_3$—$CH_3$) and propane ($CH_3$—$CH_2$—$CH_3$) have no isomers, butane has two, pentane has 3 and so forth. The number of theoretical couples becomes tremendous with higher hydrocarbons.

According to one embodiment of the invention, a concentration difference of one or all the isomers in the feed may be maintained by using a third component at the other (permeate) side of the membrane, or by applying a partial or complete vacuum at the other (permeate) side. The above and other characteristics and advantages of the invention will be better understood through the following illustrative end non-limitative description of preferred embodiments.

EXAMPLES

In all of the following Examples the permeability characteristics of the membrane with regard to a particular gas are described in terms of permeance, which is defined as the flux of that gas [STP volume or moles/(unit area x unit lime)] per unit of driving force, usually that gas's partial pressure difference across the membrane. In this examples the units employed are $l(STP)\ m^{-2}hr^1atm^{-1}$.

Figure 3:
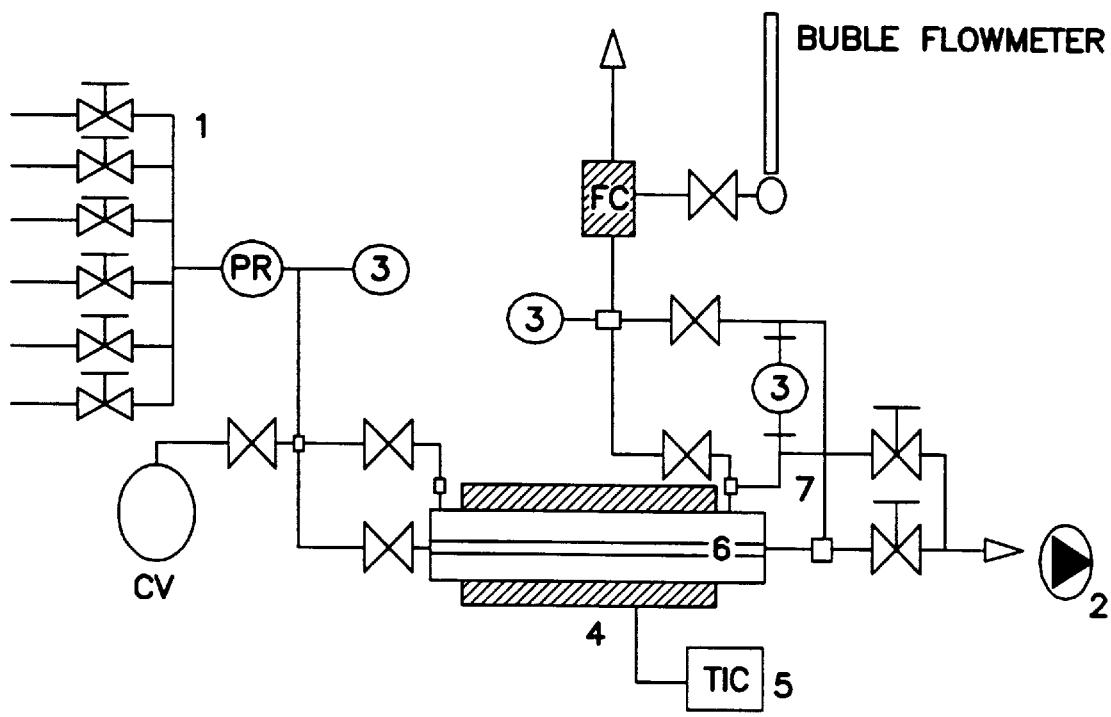
FIG. 3 shows an apparatus for tailoring pore size of carbon molecular sieve membrane.
Figure 4:
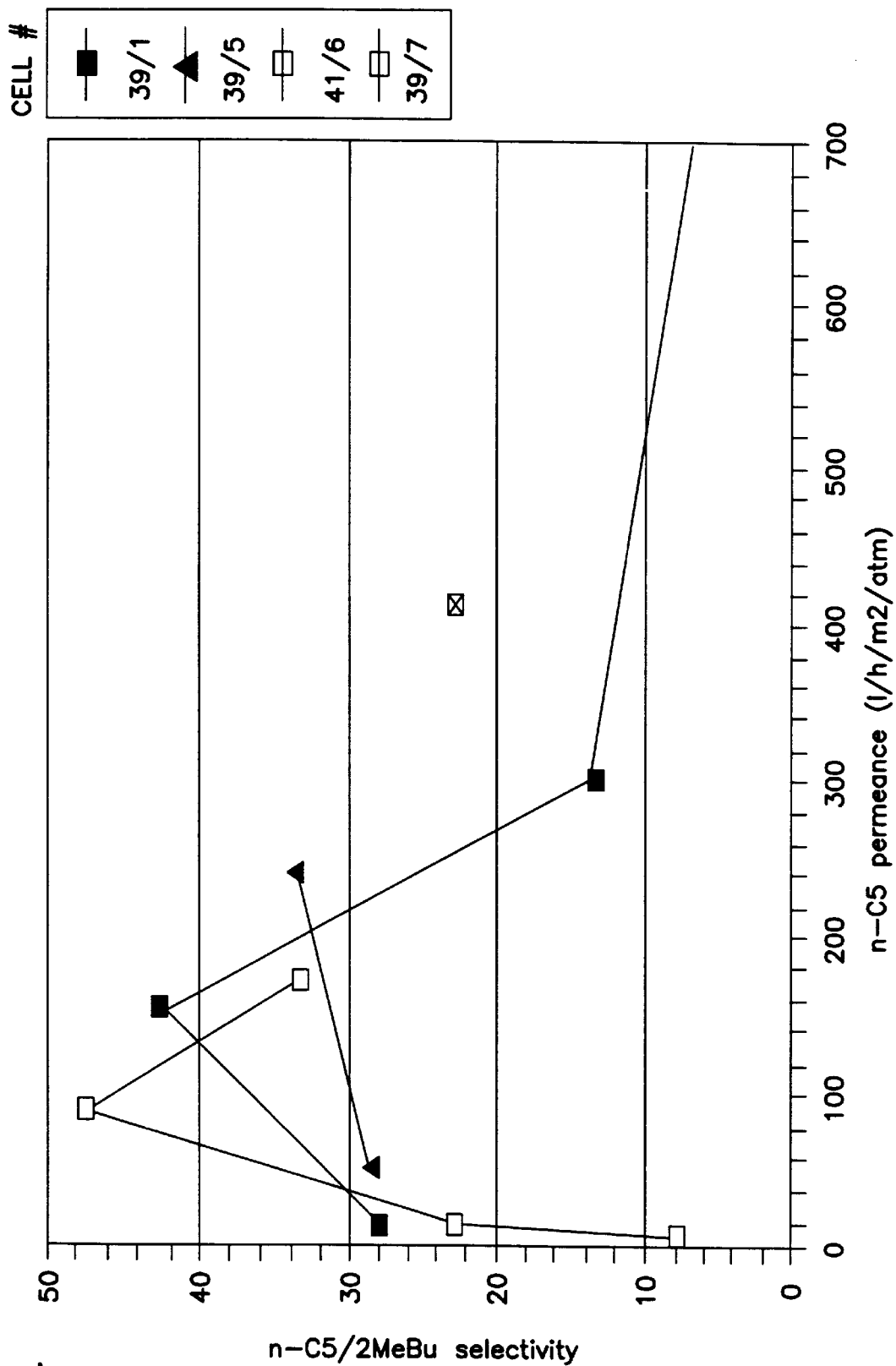
FIG. 4 is a plot of ideal permeance-selectivity parameters of CMSM membranes prepared for n-C5/i-C5 separations.

The membrane pore tailoring is done in an apparatus that can be represented by the flow sheet in FIG. 3. It provides a feed manifold (1) with appropriate valving and piping to allow controlled rate of flow of the gases used for the various termochemical treatments, a vacuum pump (2) for removing gases of the previous thermochemical step before introducing those of the next step, pressure gauges (3) for monitoring feed and permeate side gas pressures, and an oven (4) with temperature indicator and controller (TIC-5) for controlling the temperature of the membrane in the presence of the flowing gases, and the membrane module itself (6) which is connected to the feed manifold (1), permeate manifold (7) and the vacuum pump (2) by appropriate valving and piping. In addition, the following elements are shown: CV(calibrated volume), PR(pressure regulator), FC(flow controller).

Example 1

Tailoring membranes to separate between N-C5 and I-C5

Carbon membranes produced by carbonizing a non-melting, such as a cellulosic membrane in a controlled atmosphere and a programed temperature changed scheme was processed according to the thermochemical treatment detailed in Table II. In the Table "Neo" stands for 2,2-dimethyl propane, "n-C5" stands for n-pentane, "2MeBu" stands for 2-methyl butane, "Vac" means that a vacuum was applied, and "$H_2/N_2$" and "$O_2/N_2$" indicate the selectivity of hydrogen and of oxygen, relative to nitrogen respectively.

Permeances of the gases in mixture to be separated (n-C5/2MeBu) are reported in the Table, along with the calculated selectivity and the permeances of oxygen, nitrogen and hydrogen, as well as their relative selectivities. From the results it is evident from the permeance data on lines 7,8 that a membrane of good oxygen/nitrogen and hydrogen/nitrogen permeabilities and selectivities shows negligibly low permeance for all the hydrocarbons isomers. On the other hand, it is seen from rows 10 and 11 that after further activation steps the separation properties (both high permeance and high selectivity) are obtained when several $O_2/H_2$ treatment steps are applied, and that this membrane has low selectivity for oxygen/nitrogen or hydrogen/nitrogen separations, as compared to the properties seen on lines 7,8. This implies that a membrane suitable for isomer separation is of totally different properties than a membrane suitable for separating hydrogen and oxygen from nitrogen.

Comparing the results shown on lines 10 and 11 with those shown in lines 13 and 14, it is seen that upon further thermochemical treatment cycles of $O_2/H_2$, the permeance of all gases tested increases at the expense of selectivity. While the permeance-selectivity values for the pentane isomers of lines 11 and 14 are of interest for isomer separation, those of line 8 are too low in permeance.

It is seen that the production of an isomer separating membrane requires a certain variety of specific thermochemical treatments. Following the permeance-selectivity results of is example step by step indicates that $O_2/H_2$ treatments increases permeance and decreases selectivity, while the treatment with 2,2-dimethyl propane brings about the opposite.

TABLE II

| | | | | | | Measurements permeance ($l\ m^{-2}\ h^{-1}\ atm^{-1}$) | | | | | | | |
|---|---|---|---|---|---|---|---|---|---|---|---|---|---|
| Step | Tem. | | P(atm) | | time | | | select. n-C5/ | | | | select. | select. |
| No. | (° C.) | gas | in | out | (min) | n-C5 | 2-MeBu | 2-MeBu | O2 | N2 | H2 | $H_2/N_2$ | $O_2/N_2$ |
| 1 | 280 | O2 | 1 | 1 | 75 | | | | | | | | |
| 2 | 620 | H2 | 1 | 1 | 12 | | | | 1566 | 1300 | | | |
| 3 | 700 | Neo | 1 | Vac | 3 | | | | 4.3 | | 78 | | |
| 4 | 280 | O2 | 1 | 1 | 20 | | | | | | | | |
| 5 | 620 | H2 | 1 | 1 | 10 | | | | 66.4 | 12.3 | 935 | 76 | 5.4 |
| 6 | 280 | O2 | 1 | 1 | 10 | | | | | | | | |
| 7 | 620 | H2 | 1 | 1 | 10 | | | | 425 | 84 | 2070 | 24.6 | 5.06 |
| 8 | | | | | | 14 | 0.5 | 28 | | | | | |
| 9 | 260 | O2 | 1 | 1 | 30 | | | | | | | | |
| 10 | 620 | H2 | 1 | 1 | 10 | | | | 1062 | 504 | 2588 | 5.18 | 2.11 |
| 11 | | | | | | 149 | 3.5 | 42.57 | | | | | |
| 12 | 260 | O2 | 1 | 1 | 30 | | | | | | | | |
| 13 | 620 | H2 | 1 | 1 | | | | | 1294 | 744 | 2921 | 3.98 | 1.74 |
| 14 | | | | | | 299 | 22.6 | 13.28 | | | | | |

Tables III–V reinforce this conclusion, for three additional membrane samples, i.e. that whereas the $O_2/N_2$ selectivity has been reduced by successive activations to a range of 1.2-2.2, the n-pentane/2 MeBu selectivity has increased to a range of 13–47

TABLE III

Measurements
permeance (l m$^{-2}$ h$^{-1}$ atm$^{-1}$)

| Step No. | Tem. (° C.) | gas | P(atm) in | P(atm) out | time (min) | n-C5 | 2-MeBu | select. n-C5/ 2-MeBu | O2 | N2 | H2 | select. H$_2$/N$_2$ | select. O$_2$/N$_2$ |
|---|---|---|---|---|---|---|---|---|---|---|---|---|---|
| 1 | 280 | O2 | 1 | 1 | 60 | | | | | | | | |
| 2 | 620 | H2 | 1 | 1 | 15 | | | | 380 | 128 | 922 | 7.2 | 2.97 |
| 3 | 700 | Neo | 1 | Vac | 3 | | | | | | | | |
| 4 | 280 | O2 | 1 | 1 | 50 | | | | | | | | |
| 5 | 620 | H2 | 1 | 1 | 15 | | | | 738 | 415 | 1695 | 4.08 | 1.78 |
| 6 | | | | | | 43 | 4.6 | 9.848 | | | | | |
| 7 | 280 | O2 | 1 | 1 | 20 | | | | | | | | |
| 8 | 620 | H2 | | | | | | | 968 | 691 | 1705 | 2.47 | 1.4 |
| 9 | 200 | Neo | 1 | 1 | 60 | | | | | | | | |
| 10 | | | | | | 105 | 17 | 6.176 | | | | | |
| 11 | 280 | O2 | 1 | 1 | 20 | | | | | | | | |
| 12 | 620 | H2 | 1 | 1 | 5 | | | | 1230 | 976 | | | 1.26 |
| 13 | | | | | | 827 | 49 | 16.88 | | | | | |

TABLE IV

Measurements
permeance (l m$^{-2}$ h$^{-1}$ atm$^{-1}$)

| Step No. | Tem. (° C.) | gas | P(atm) in | P(atm) out | time (min) | n-C5 | 2-MeBu | select. n-C5/ 2-MeBu | O2 | N2 | H2 | select. H$_2$/N$_2$ | select. O$_2$/N$_2$ |
|---|---|---|---|---|---|---|---|---|---|---|---|---|---|
| 1 | 280 | O2 | 1 | 1 | 40 | | | | | | | | |
| 2 | 620 | H2 | 1 | 1 | 10 | | | | 344 | 48 | 960 | 20 | 7.17 |
| 3 | 280 | O2 | 1 | 1 | 15 | | | | | | | | |
| 4 | 620 | H2 | 1 | 1 | | | | | 980 | 550 | 1805 | 3.28 | 1.78 |
| 5 | | | | | | 50 | 1.75 | 28.57 | | | | | |
| 6 | 200 | Neo | Vac | 1 | 60 | | | | 643 | 295 | | | 2.18 |
| 7 | 680 | O2 | 1 | 1 | 25 | | | | | | | | |
| 8 | 620 | H2 | 1 | 1 | 10 | | | | 1167 | 872 | | | 1.84 |
| 9 | | | | | | 236 | 7 | 33.71 | | | | | |

TABLE V

Measurements
permeance (l m$^{-2}$ h$^{-1}$ atm$^{-1}$)

| Step No. | Tem. (° C.) | gas | P(atm) in | P(atm) out | time (min) | n-C5 | 2-MeBu | select. n-C5/ 2-MeBu | O2 | N2 | H2 | select. H$_2$/N$_2$ | select. O$_2$/N$_2$ |
|---|---|---|---|---|---|---|---|---|---|---|---|---|---|
| 1 | 280 | O2 | 1 | 1 | 90 | | | | 3.4 | 0.7 | | | 4.86 |
| 2 | 620 | HAr | 1 | 1 | 10 | | | | 702 | 359 | | | 1.96 |
| 3 | 280 | O2 | 1 | 1 | 60 | | | | | | | | |
| 4 | 620 | HAr | 1 | 1 | 10 | | | | 1489 | 1089 | | | 1.37 |
| 5 | 700 | Neo | 1 | Vac | 3 | | | | 2.8 | 0.6 | | | 4.67 |
| 6 | 250 | O2 | 1 | 1 | 60 | | | | | | | | |
| 7 | 620 | HAr | 1 | 1 | 10 | | | | 9 | 2 | | | 4.5 |
| 8 | 280 | O2 | 1 | 1 | 30 | | | | | | | | |
| 9 | 620 | HAr | 1 | 1 | 10 | | | | 28 | 5 | | | 5.6 |
| 10 | 800 | O2 | 1 | 1 | 45 | | | | | | | | |
| 11 | 620 | HAr | 1 | 1 | 10 | | | | 234 | 32 | 1380 | 43.1 | 7.31 |
| 12 | 280 | O2 | 1 | 1 | 60 | | | | | | | | |
| 13 | 620 | HAr | 1 | 1 | 10 | | | | 726 | 234 | 2058 | 8.79 | 3.1 |
| 14 | | | | | | 5.4 | 0.7 | 7.714 | | | | | |
| 15 | 260 | O2 | 1 | 1 | 30 | | | | | | | | |
| 16 | 620 | HAr | 1 | 1 | 10 | | | | 1001 | 456 | | | 2.2 |
| 17 | | | | | | 1.6 | 0.7 | 22.86 | | | | | |
| 18 | 260 | O2 | 1 | 1 | 30 | | | | | | | | |
| 19 | 620 | HAr | 1 | 1 | 10 | | | | 1162 | 690 | | | 1.68 |
| 20 | | | | | | 85 | 1.8 | 47.22 | | | | | |

TABLE V-continued

| Step No. | Tem. (° C.) | gas | P(atm) in | P(atm) out | time (min) | n-C5 | 2-MeBu | select. n-C5/ 2-MeBu | O2 | N2 | H2 | select. $H_2/N_2$ | select. $O_2/N_2$ |
|---|---|---|---|---|---|---|---|---|---|---|---|---|---|
| | | | | | | | | Measurements permeance $(1\ m^{-2}\ h^{-1}\ atm^{-1})$ | | | | | |
| 21 | 260 | O2 | 1 | 1 | 45 | | | | | | | | |
| 22 | 620 | HAr | 1 | 1 | 10 | | | | 1210 | 835 | | | 1.45 |
| 23 | | | | | | 167 | 5 | 33.4 | | | | | |

Example 2 n-C5/i-C5 Selectivity achieved without CVD

This example uses a different thermochemical treatment route as shown in Table VI. As can be seen, even though no CVD step is used, but only activation and reduction steps, a practical permeance for n-C5 is achieved (410 l $m^{-2}\ hr^{1}\ atm^{-1}$) with excellent selectivity (>20).

TABLE VI

| Step No. | Tem. (° C.) | gas | P(atm) in | P(atm) out | time (min) | n-C5 | 2-MeBu | select. n-C5/ 2-MeBu | O2 | N2 | H2 | select. $H_2/N_2$ | select. $O_2/N_2$ |
|---|---|---|---|---|---|---|---|---|---|---|---|---|---|
| | | | | | | | | Measurements permeance $(1\ m^{-2}\ h^{-1}\ atm^{-1})$ | | | | | |
| 1 | 280 | O2 | 1 | 1 | 75 | | | | | | | | |
| 2 | 620 | HAr | 1 | 1 | 10 | | | | 1088 | 575 | 1843 | 3.21 | 1.89 |
| 3 | 260 | O2 | 1 | 1 | 30 | | | | | | | | |
| 4 | 620 | HAr | 1 | 1 | 10 | | | | 1735 | 1118 | 2824 | 2.53 | 1.55 |
| 5 | 620 | | | | | 410 | 18 | 22.78 | | | | | |

Example 3

Results from Actual Mixtures of N-C5/2-MeBu

While Examples 1 and 2 used permeance measurements on pure isomer gases to obtain calculated ideal selectivities, there was some concern that certain effects would interfere with achieving his selectivity in separations of actual mixtures. The separation of hydrocarbon mixes is complicated by the fact that they are much easier to liquefy than noble or air-like gases. As a result, if feed temperature and pressure conditions are not sufficiently far from those needed for liquefaction, partial condensation of components of the gas mixture can occur within the pores of the membrane, even though the mixture remains a gas in the feed. This can even result in the less permeable component condensing and preventing passage of the more permeable component. This Example demonstrates practicality of operating the membrane with mixtures to attain selectivities approaching those calculated from pure gas permeances.

Figure 5:
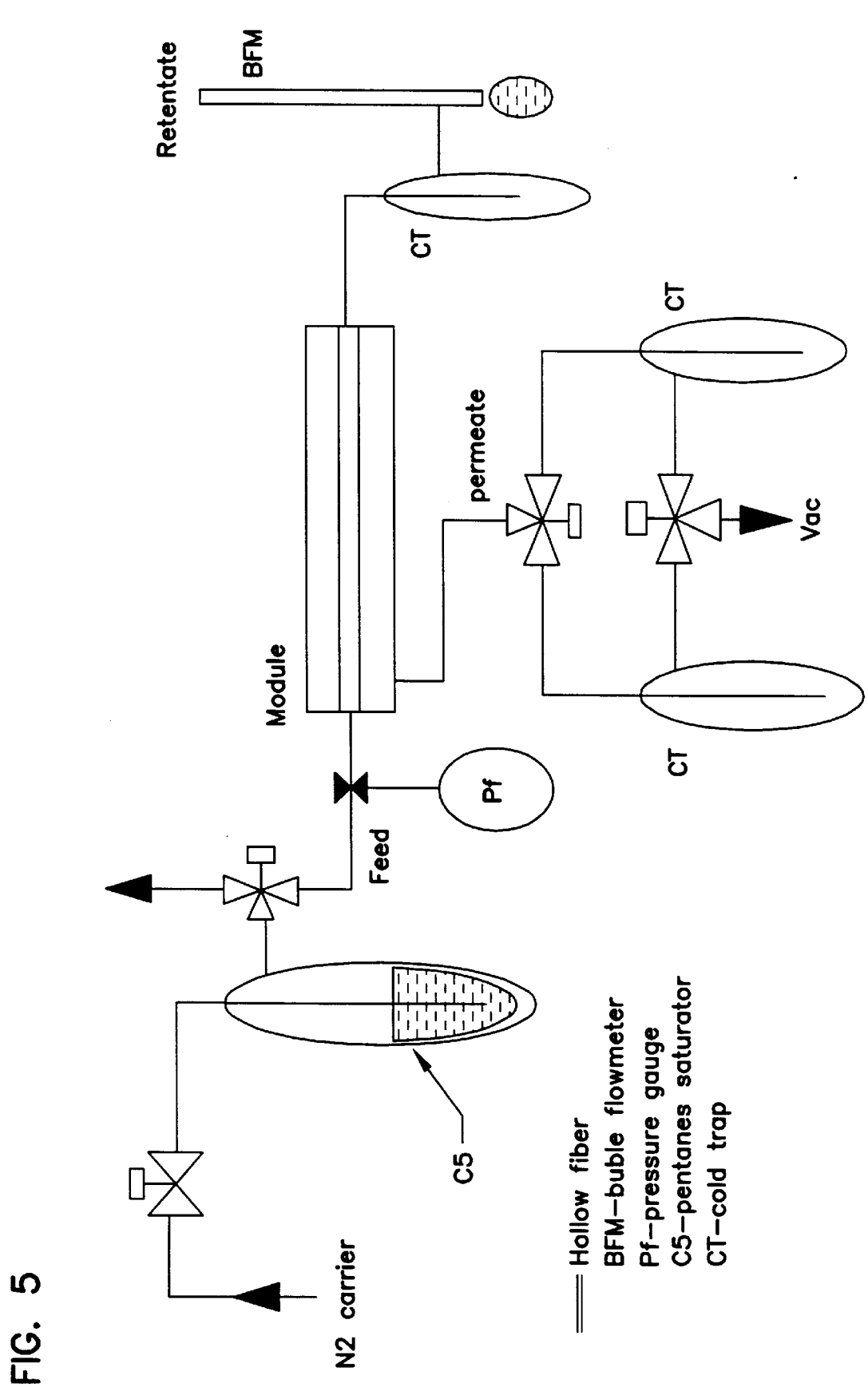
FIG. 5 shows the test apparatus for measuring performance of CMSM on pentane isomer mixtures.

The experimental setup was as follows:

The module was tested in the apparatus shown in FIG. 5 to measure permeance and selectivity in the presence of mixtures of pentane isomers. The same apparatus could be used for measuring the permeance of the pure isomers and for measuring mixtures of other alkanes (eg C3–C10) as well.

Figure 6:
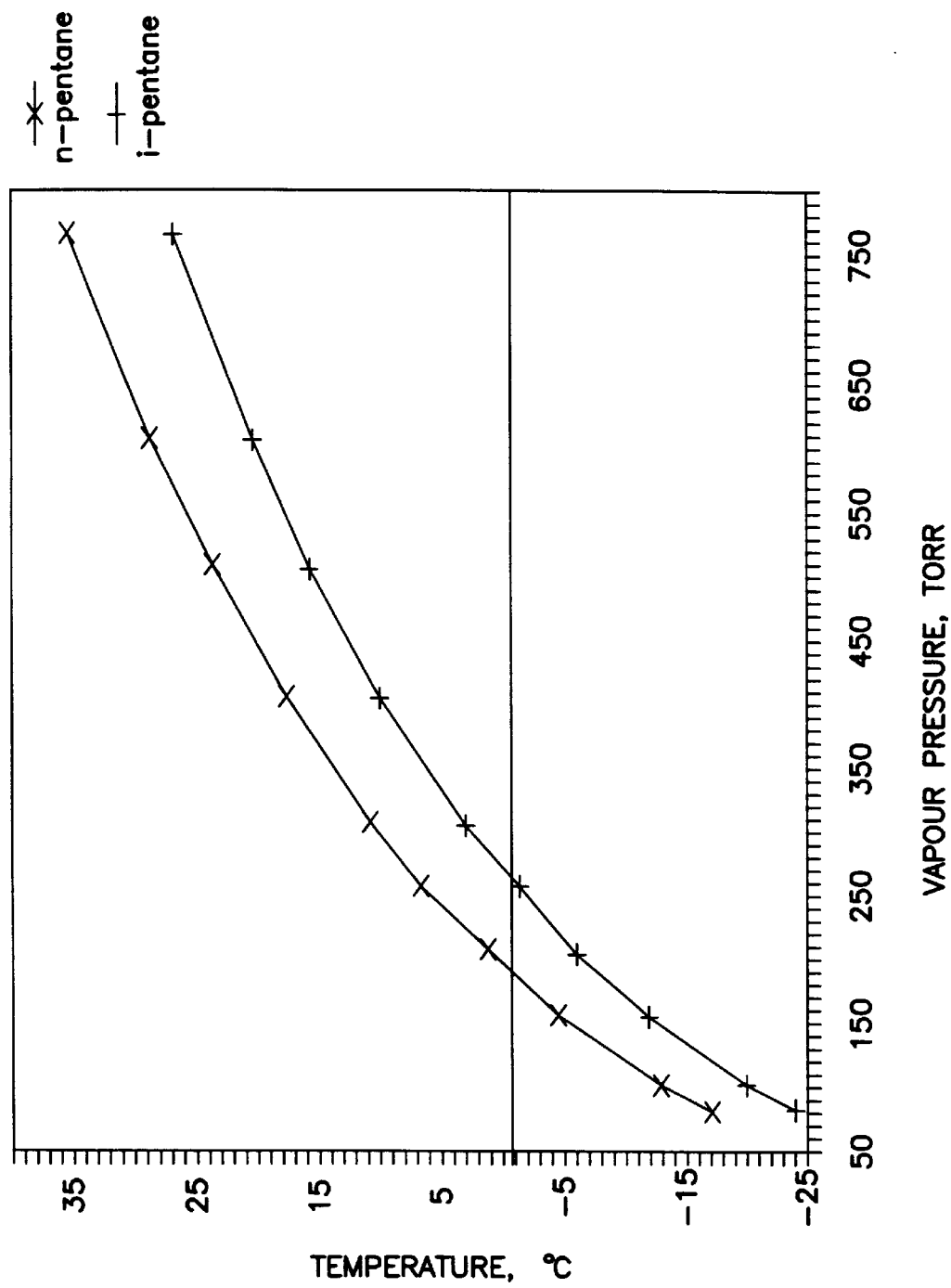
FIG. 6 shows the vapor pressures for n-pentane and i-pentane as function of temperatures.

In order not to consume large quantities of the pentane mixture during the course of the experiment, the liquid mixture was kept at 0° C. to maintain a relatively low vapor pressure. The graph of pentane vapor pressure as a function of temperature is provided in FIG. 6 as a reference. The C5 isomer mixture vapor was transported to the membrane module by a nitrogen sweep gas. In these experiments the feed was on the bore side of the module. A pressure gauge (Pf) was used to measure the total pressure of the feed gas and a bubble flow meter (BFM) was used to measure the flow rate of the sweep gas in the retentate after removal of the condensible hydrocarbons. A similar arrangement was made to measure the nitrogen flow rate in the feed stream. From a knowledge of the total pressure of the feed gas stream and the vapor pressure of the pentanes the partial pressures of all components could be calculated.

A vacuum was pulled on the permeate side to provide driving force. The isomer mixture in feed, retentate and permeate streams could each be condensed in a cold trap (CT) for subsequent analysis in a gas chomatograph to establish the composition of each stream. The flow rate of the isomer mixture in each stream was determined by measuring the accumulated weight change in the cold trap for a determined period of time. The condensed pentane isomers were then mixed with a high boiling diluent (dodecane) to prevent evaporation and compositional changes before delivering the samples for gas chromatography.

In actual practice a stream composed of hydrocarbons without the sweep gas hydrocarbon stream the module temperature must be maintained at a temperature at which the equilibrium vapor pressure of the pentane isomers exceeds the operating pressure in order to prevent condensation in the pores and loss of penneability. In this work the module was maintained at elevated temperatures (80–140° C.) by a cylindrical oven around the module housing. The elevated temperature prevented condensation of the hydrocarbon in the membrane pores and promoted the rate of transmembrane transport.

Figure 7:
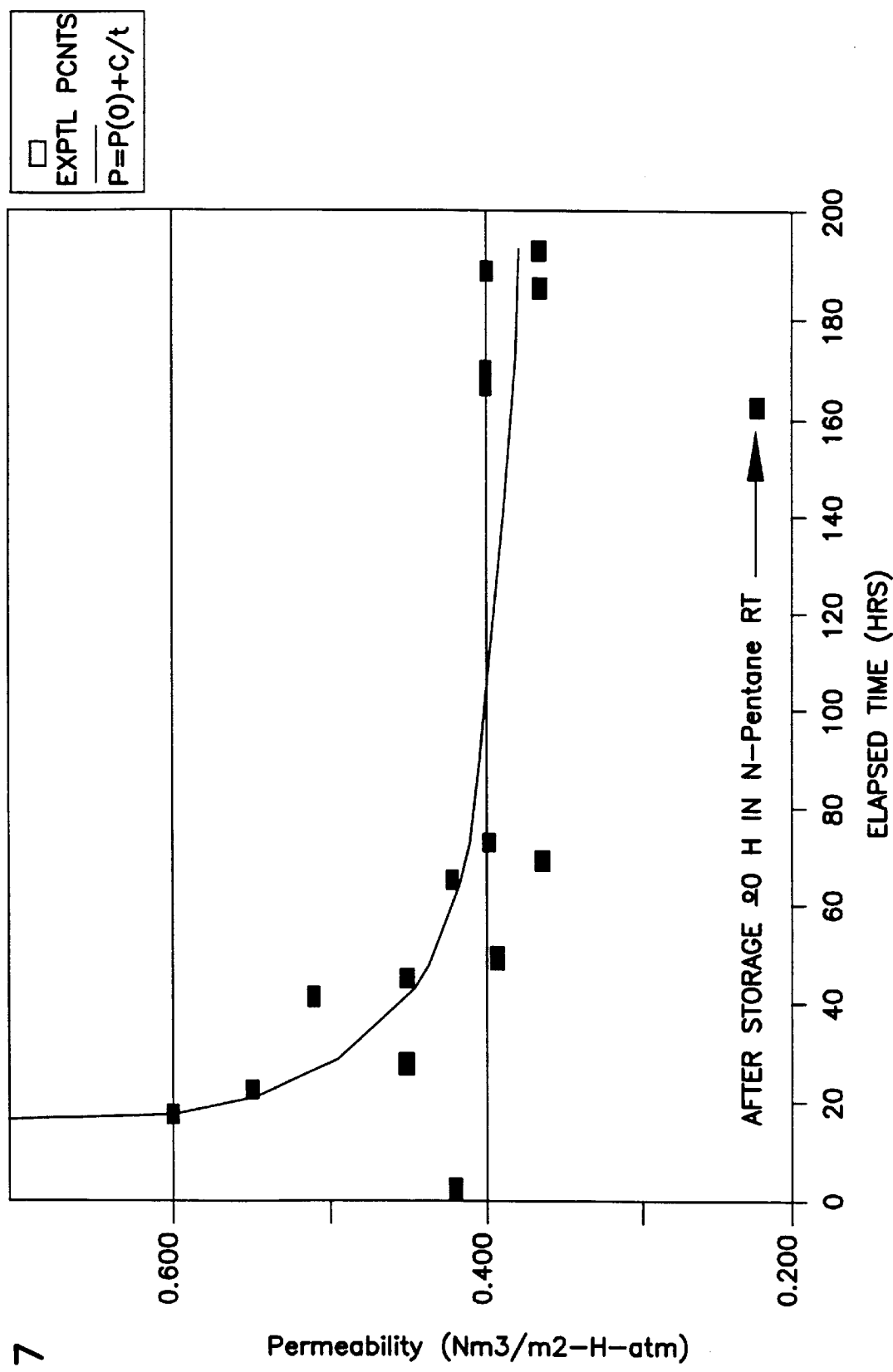
FIG. 7: illustrates the stability of isomer resolving CMSM membranes with respect to n-pentane permeance.

The raw data fox a typical experiment are provided in Table VII. The total amount of alkane in each stream was determined gravimetrically. The relative amounts of each isomer were determined on a GC. By converting all raw data into molar flows they were reduced to the mass balance summary found in Table VIII. The molar flow of nitrogen in the permeate was not measured but calculated by difference between feed and retentate assuming 100% mass balance for nitrogen. The driving force for pentane permeation was calculated from its partial pressure in the feed stream allowing for the axial pressure drop. The permeate pressure was negligible under vacuum. From the permeation rate for each of the isomers and the partial pressure driving force, the permeance and selectivity was calculated for each isomer.

the module as described in Example 3. The temperature was maintained at 80° C. Periodically the permeance was measured. The results of this test are given in FIG. 7.

EXAMPLE 5

This Example shows how the selectivity is greatly increased as the size difference between the two isomers increases. Neopentane differs from n-pentane by about 1.2 Angstroms in its smallest molecular dimension. This compares with a difference of only about 0.4 Angstroms between isopentane (i.e. 2-methyl butane) and n-pentane.

A hollow fiber made from pyrolyzing a non-melting polymer, with a wall of 10 $\mu$m thickness was processed according to the thermochemical treatment detailed in Table VII. Permeance of the gases to be separated (n-C5/Neo) are reported in the Table, along with the calculated selectivity

TABLE VII

Temperature of Pentane Reservoir: 0° C.
Reservoir Isomer Ratio (n-C5:i-C5): 70:30
Diluent in permeate/Retentate Trap: dodecene
Membrane T 100° C.
P°(0°) n-C5 = 185 torr             # of fibers 10
P°(0°) 2-MeBu = 259 torr           Length, cm 9

| exp.# 5a | alkene net mgr | sample time min | CARRIER Gas Flow ccNTP/ min | total press (torr) | added diluent cc | GC mg n-C5 | GC mg 2MeBu | true mg n-C5 | true mg 2MeBu | part. press. (torr) n-C5 | part. press. (torr) 2MeBu |
|---|---|---|---|---|---|---|---|---|---|---|---|
| FEED | 100.8 | 3.9 | 36.7 | 817 | 5 | 67.5 | 41 | 62.7 | 38.1 | 98.1 | 59.6 |
| PERM | 47.4 | 64 | 0 | 0 | 5 | 39 | 1.5 | 45.6 | 1.8 | 0.0 | 0.0 |
| REJE | 90.9 | 3.57 | 34 | 720 | 5 | 54 | 34 | 55.8 | 35.1 | 89.6 | 56.4 |

TABLE VIII

Summary of separation of pentane isomer mixture.
EXPT 5a: Mixed Pentanes in N2 Carrier St

| STREAM: Component | Feed | Permeate ←Jv(Mol m$^{-2}$H$^{-1}$)→ Retentate | | % CUT | MASS BALANCE | Permeance (Sl m$^{-2}$H$^{-1}$Ar$^{-1}$) |
|---|---|---|---|---|---|---|
| n-pentane | 28.69 | 1.27 | 27.88 | 4.4% | 101.6% | 230.9 |
| iso-pentane | 17.43 | 0.05 | 17.55 | 0.2% | 101.0% | 14.4 |
| N2 Carrier | 192.84 | 14.19 | 178.65 | 7.4% | 100.0% | 391.7 |
| TOTAL | 225.44 | 15.51 | 224.09 | 6.9% | 106.8% | |

SELECTIVITY (n/iso): 16.1

Example 4

This Example shows the membrane permeance for n-pentane is stable over practical lengths of operating time. A stream of pentane in nitrogen carrier gas was fed through and the fluxes of oxygen, nitrogen and hydrogen, as well as their relative selectivities. From the results in the Table it is seen that excellent n-C5/Neo selectivity is obtained at the end of the treatment.

TABLE IX

Measurements
permeance (l m$^{-2}$ h$^{-1}$ atm$^{-1}$)

| Step No. | Tem. (° C.) | gas | P(atm) in | P(atm) out | time (min) | n-C5 | 2-MeBu | select. n-C5/ 2-MeBu | O2 | N2 | H2 | select. H$_2$/N$_2$ | select. O$_2$/N$_2$ |
|---|---|---|---|---|---|---|---|---|---|---|---|---|---|
| 1 | 280 | O2 | 1 | 1 | 60 | | | | 914 | 408 | | | 2.24 |
| 2 | 620 | HAr | 1 | 1 | 10 | | | | | | | | |
| 3 | 260 | O2 | 1 | 1 | 60 | | | | 1670 | 1178 | | | 1.42 |
| 4 | 620 | HAr | 1 | 1 | 10 | | | | | | | | |
| 5 | 280 | O2 | 1 | 1 | 20 | | | | 2028 | 1610 | | | 1.26 |
| 6 | 800 | HAr | 1 | 1 | 80 | | | | | | | | |
| 7 | 280 | O2 | 1 | 1 | 15 | | | | 2296 | 1908 | | | 1.2 |
| 8 | 620 | HAr | 1 | 1 | 10 | | | | | | | | |
| 9 | 280 | O2 | 1 | 1 | 15 | | | | 2525 | 2505 | | | 1.01 |
| 10 | 620 | HAr | 1 | 1 | 10 | | | | 2147 | 2087 | | | 1.03 |
| 11 | | | | | | 1280 | 0.6 | 2183 | | | | | |

Example 6

Example shows that the membrane power to separate isomers is not limited to C5 isomers but is general for straight vs. branched chain hydrocarbons, as described in the invention. In this Example the membrane selectivity between n-butane and i-butane is demonstrated.

The membrane was prepared in a similar manner to that in Example 1 and the pure gas permeances were measured after each activation at 80° C. The results are given in Table X.

TABLE X

Ideal Permeances for C4 isomers for CMSM cell #1578/3

| Preparation step | Permeances (L(STP)/M2-Hr/Atm) | | |
|---|---|---|---|
| | n-C4 | iso C4 | ideal S |
| 1st activation | 82 | 1.4 | 59 |
| 2nd activation | 320 | 9.1 | 35 |
| 3rd activation | 510 | 26 | 19.6 |

Example 7

In the above Example it was found that the measured values of the permeance of n-butane after i-butane were lower than if n-butane alone were measured. This reinforced the concern about adsorption/condensation of the hydrocarbons if the temperatures were not kept above the condensation point. Therefore in this example, mixtures of butane isomers were measured to show the practical effectivness of the invention in separating actual mixtures.

The modules were prepared as described in the previous examples. The testing apparatus used was similar to that shown in FIG. 5 with the following modifications:

The N$_2$ carrier gas and liquid reservoir arrangement were eliminated. Instead CP i-butane and n-butane were fed separately from lecture bottles and mixed in the manifold where they were then fed into the module. Permeate was accumulated in a cold trap (CT). Its quantity was determined by evaporating and expanding the condensed gas into a previously evacuated calibrated volume at room temperature. From the pressure the quantity of gas mixture was determined, using the equation of state for gases (n=PV)RT). Removable sample traps of permeate and retentate streams were submitted for GC analysis as were samples of the feed stream. The results of runs on two different samples are shown in Tables XI and XII. They demonstrate the striking performance of the CMSM membrane in effecting the separation.

All the above description and examples have been provided for the purpose of illustration, and are not intended to limit the invention in any way.

TABLE XI

| Temp | # of fibers | | 2 | | | | | | | | |
|---|---|---|---|---|---|---|---|---|---|---|---|
| 100° C. | length, cm | | 25.8 | | | | | | | | |

| exp. #2 | trap Vol (cc) | trap pressure (Torr) | sample time (min) | Gas Flow (ccSTP/ min) | total press. (torr) | by GC X nC4 | by GC 1-X iC4 | partial press. (torr) n-C4 | partial press. (torr) i-C4 | SLm$^{-2}$h$^{-1}$atm$^{-1}$ n-C4 | SLm$^{-2}$h$^{-1}$atm$^{-1}$ i-C4 | select. |
|---|---|---|---|---|---|---|---|---|---|---|---|---|
| Feed: | | 870 | | 6.97 | 870 | 60.1% | 59.7% | 523 | 345 | | | |
| Perm: | 37.7 | 365 | 31 | 0.56 | 0 | 96.9% | 2.6% | 0 | 0 | 219.7 | 9.1 | 24.2 |
| reject | 10 | 720 | 30 | 6.47 | 720 | 61.2% | 38.6% | 441 | 278 | | | |

TABLE XII

Temp 100° C.  # of fibers 2  length, cm 29

| exp. #3 | trap Vol (cc) | trap pressure (Torr) | sample time (min) | Gas Flow (ccSTP/min) | total press. (torr) | by GC X nC4 | by GC 1-X iC4 | partial press. (torr) n-C4 | partial press. (torr) i-C4 | SLm⁻²h⁻¹atm⁻¹ n-C4 | SLm⁻²h⁻¹atm⁻¹ i-C4 | select. |
|---|---|---|---|---|---|---|---|---|---|---|---|---|
| Feed. | | 863.326 | | 8.03 | 870 | 26.0% | 74.0% | 226 | 644 | | | |
| Perm: | 37.7 | 510 | 30.5 | 0.76 | 0 | 85.3% | 14.7% | 0 | 0 | 683.4 | 36.5 | 19.3 |
| reject | 10 | 720 | 30 | 7.27 | 720 | 19.7% | 80.3% | 142 | 578 | | | |

We claim:

1. A method for the separation of linear from branched hydrocarbon isomers, comprising the steps of:

selecting a carbon membrane having a pore size, comprised in the range 3.9 Å to 5.5 Å;

providing a separating means between the two sides of the membrane, so that hydrocarbon molecules cannot move from one side of the membrane to the other, save through the membrane;

providing a mixture of two isomers to be separated and bringing the said mixture into contact with a mixture feed side of the membrane;

applying a driving force across the membrane;

collecting a permeate richer in the isomer having the smaller size from a permeate side of the membrane opposite to said mixture feed side; and collecting a retentate richer in the isomer having the larger size from said mixture feed side of the membrane.

2. A process according to claim 1, wherein the feed mixture of isomers is kept in the gaseous state.

3. A process according to claim 1, wherein a concentration difference of one or all the isomers in the feed is maintained by applying a partial or complete vacuum at the permeate side of the membrane.

4. A process according to claim 1, wherein the isomers to be separated are selected from normal hydrocarbons and hydrocarbons containing secondary, tertiary or ternary carbon atoms.

5. A method for the separation of linear from branched hydrocarbon isomers, comprising the steps of:

selecting a carbon membrane having a pore size, comprised in the range 3.9 Å to 5.5 Å;

providing separating means between the two sides of the membrane, so that hydrocarbon molecules cannot move from one side of the membrane to the other, save through the membrane;

providing a mixture of two isomers to be separated and bringing the said mixture into contact with a mixture feed side of the membrane;

providing a pressure drop across the membrane, the higher pressure being on the mixture side thereof;

collecting a permeate richer in the isomer having the smaller size from the permeate side of the membrane opposite to said mixture feed side; and collecting a retentate richer in the isomer having the larger size from said mixture feed side of the membrane.

* * * * *